(12) United States Patent
Gerlach et al.

(10) Patent No.: US 8,190,464 B2
(45) Date of Patent: May 29, 2012

(54) METHOD AND APPARATUS FOR IDENTIFYING AND CONTACTING CUSTOMERS WHO ARE DUE FOR A VISIT BUT HAVE NOT SCHEDULED AN APPOINTMENT

(75) Inventors: Brett C. Gerlach, Riverton, UT (US); Brian William Perrin, American Fork, UT (US)

(73) Assignee: Brevium, Inc., Eagle Mountain, UT (US)

( * ) Notice: Subject to any disclaimer, the term of this patent is extended or adjusted under 35 U.S.C. 154(b) by 1122 days.

(21) Appl. No.: 11/484,340

(22) Filed: Jul. 10, 2006

(65) Prior Publication Data
US 2008/0306781 A1 Dec. 11, 2008

(51) Int. Cl.
*G06Q 10/00* (2006.01)
(52) U.S. Cl. ............... 705/7.18; 705/7.12; 705/7.13; 705/7.19; 705/7.21
(58) Field of Classification Search ............... 705/7.12, 705/13, 18, 19, 21
See application file for complete search history.

(56) References Cited

U.S. PATENT DOCUMENTS

| | | | | |
|---|---|---|---|---|
| 5,483,443 | A * | 1/1996 | Milstein et al. | 705/3 |
| 5,557,514 | A * | 9/1996 | Seare et al. | 705/2 |
| 5,737,726 | A * | 4/1998 | Cameron et al. | 705/7.21 |
| 5,918,208 | A * | 6/1999 | Javitt | 705/2 |
| 5,982,863 | A * | 11/1999 | Smiley et al. | 379/88.18 |
| 6,024,699 | A * | 2/2000 | Surwit et al. | 600/300 |
| 6,680,999 | B1 * | 1/2004 | Garcia | 379/88.22 |
| 7,702,522 | B1 * | 4/2010 | Sholem | 705/2 |
| 7,774,210 | B1 * | 8/2010 | Sandberg | 705/2 |
| 2001/0056356 | A1 * | 12/2001 | Waters et al. | 705/2 |
| 2002/0138306 | A1 | 9/2002 | Sabovich | |
| 2002/0156672 | A1 | 10/2002 | Burko | |
| 2002/0191035 | A1 * | 12/2002 | Selent | 345/866 |
| 2003/0120512 | A1 * | 6/2003 | Dengler | 705/2 |
| 2003/0179223 | A1 * | 9/2003 | Ying et al. | 345/702 |
| 2003/0195774 | A1 * | 10/2003 | Abbo | 705/3 |
| 2004/0019501 | A1 | 1/2004 | White et al. | |
| 2004/0181433 | A1 | 9/2004 | Blair | |
| 2004/0199406 | A1 * | 10/2004 | Owens et al. | 705/2 |
| 2004/0243436 | A1 * | 12/2004 | Rawat et al. | 705/2 |
| 2005/0234739 | A1 * | 10/2005 | Schoenberg | 705/2 |

(Continued)

OTHER PUBLICATIONS

Health Systems Management Group."Medical Practice Expert Software Features." <http://web.archive.org/web/20050324141543/www.hsmg.biz/cal.med.features.html>.*

(Continued)

*Primary Examiner* — R. David Rines
*Assistant Examiner* — Renae Feacher
(74) *Attorney, Agent, or Firm* — Scheinberg & Griner, LLP; Michael O. Scheinberg; John Kelly (57) ABSTRACT

A management database is queried to determine which customers have failed to respond to recall notices. The resulting list of customers may be sorted or filtered so that some customers are preferentially contacted first, based on expected value or office preferences. The list may also be sorted or filtered to fill specific providers' schedules first. Customer names and contact information are then presented to schedulers so that customers may be contacted. The time and date of each contact is automatically recorded along with the outcome of the contact. A customer name is presented to a scheduler only if the same name is not being simultaneously presented to other schedulers and that customer was not too recently contacted, so that redundant or too frequent contacts are avoided.

27 Claims, 5 Drawing Sheets

U.S. PATENT DOCUMENTS

| | | | |
|---|---|---|---|
| 2006/0047552 A1* | 3/2006 | Larsen et al. | 705/8 |
| 2006/0047553 A1* | 3/2006 | Fuhrmann et al. | 705/8 |
| 2006/0047554 A1* | 3/2006 | Larsen et al. | 705/8 |
| 2006/0053044 A1 | 3/2006 | Kurian et al. | |
| 2007/0078697 A1* | 4/2007 | Nixon | 705/9 |
| 2009/0094054 A1 | 4/2009 | Perrin et al. | |
| 2009/0161846 A1 | 6/2009 | Perrin et al. | |

OTHER PUBLICATIONS

CPM Marketing Group, Inc. "Life Connections." <http://web.archive.org/web/20060308193454/www.cpm.com/physicians/solutions/corecomm.cfm>.*

Frieden, Joyce."Electronic Health Records Yield Business Payoff." Internal Medicine News, vol. 39 No. 2, p. 76.*

Adams, Vicki J., Waldner, Cheryl L and Campbell, John R."Analysis of a practice management coluter software program for owner compliance with recall reminders." Can Vet J 2006; 47:234-240.*

Corey, David J. "Appointment Standardization Integrated Program Team Meeting—Activation of MCP Status." Department of Defense—Tricare Management Activity, Oct. 24, 2000.*

O'Hare, C.Dennis and Corlett, John."The Outcomes of Open-Access Scheduling." Family Practice Management, Feb. 2004, <www.aafp.org/fpm/2004/0200/p35.html>.*

Freinden, Joyce."Electronic Health Records Yield Business Payoff." Internal Medicine News, Jan. 15, 2006, p. 76, vol. 39 No. 2 ISSN: 1097-8690.*

Hashim, Muhammad Jawad, Franks, Peter and Fiscella, Kevin."Effectieness of Telephone Reminders in Improving Rate of Appointments Kept at an Outpatient Clinic: A Randomized Controlled Trial." Department of Family Medicine, University of Rochester New York, Mar. 14, 2001.*

Yedehalli Venkataramu, Raghunandan (2005). A revenue management framework for appointment allocation in rehabilitation outpatient clinics. M.S. dissertation, Wichita State University, United States—Kansas. Retrieved Jan. 5, 2012, from ABI/INFORM Global. (Publication No. AAT 1436593).*

EBSCOHost_Print Search History 01052012.*

ProQuest Search 01052012.*

Mohr, Angie."Statistics can point you in the direction of profitability." The Record (Kitchener-Waterloo, Ontario), May 4, 2005.*

11484340-381857 EICSEARCH.*

Elexity.com; 2004-2007; Elexity; retrieved Jun. 9, 2009 [www.elexity.com; http://web.archive.org/ web/20070920075315/www.elexity.com/generalSite/solutionsApptReminders.asp].

Phytel.com; 2004; Phytel; retrieved Jun. 9, 2009 [www.phytel.com; http://web.archive.org/web/20041021033228/ phytel.com/solutions/appointmentconfirmations.html].

Smilereminder.com, Webpages, 2002, Retrieved Sep. 17, 2009, [http://web.archive.org/web/20021210135102/www.smilereminder.com/index.html].

Phytel.com, Brochure, 2002, Exact publication date unknown, Retrieved Sep. 17, 2009, [http://web.archive.org/web/20030407162143/phytel.com/brochure.pdf].

Phytel.com, Webpages, 2006, Exact publication date unknown, Retrieved Sep. 17, 2009, [http://web.archive.org/web/20060813164142/http://www.phytel.com].

Phytel.com, Webpages, 2007, Exact publication date unknown, Retrieved Sep. 17, 2009, [http://web.archive.org/web/20071024121500/www.phytel.com/products/products01.htm].

Telapatient.com, "PowerCalls-DDS Appointment Confirmation System," Webpages, 1985, Exact publication date unknown, Retrieved Nov. 19, 2009, [http:/www.telapatient.com/pcalls.html], 5 pages.

American Academy of Pediatrics, "Vaccine Reminder Recall System: A Practical Guide for Pediatric Practices," Webpages, Jun. 1984, Timeline for Implementation, Aug. 1989 Complete Electronic Medical Record, [http://practice.aap.org], 5 pages.

* cited by examiner

FIG. 1

| Payor Class | Total Billings per Visit |
|---|---|
| AETNA | 101 |
| BLUE CROSS | 150 |
| MEDICARE | 64.07 |
| AETNA | 64.09 |
| AETNA | 101 |
| BLUE CROSS | 83 |
| PRIVATE | 96 |
| DSHS | 127.87 |
| PRIVATE | 0 |
| BLUE CROSS | 149.06 |
| MEDICARE | 119.72 |
| BLUE CROSS | 0 |
| PRIVATE | 425 |
| BLUE CROSS | 160 |
| AETNA | 119.72 |
| MEDICARE | 51.82 |
| DSHS | 24.8 |
| MEDICARE | 81.3 |
| BLUE CROSS | 106.3 |
| AETNA | 51.82 |
| MEDICARE | 105.37 |
| PRIVATE | 0 |
| MEDICARE | 119.72 |
| BLUE CROSS | 674.14 |
| ... | ... |

FIG. 2

| Payor Class | Average Billings per Visit |
|---|---|
| PRIVATE | 203 |
| PROVIDENCE | 190 |
| BLUE CROSS | 174 |
| AETNA | 149 |
| MEDICARE | 147 |
| HMO | 137 |
| MEDICAID | 85 |
| DSHS | 54 |

| Result of contact | Make further contact |
|---|---|
| Message left | After 1 week, no more than 3 total messages |
| No answer | After 1 day |
| Appointment made | Never |
| Appointment declined | Never |
| Appointment already scheduled | Never |
| Appointment made after message left | Never |
| Deceased or moved out of area | Never |
| Invalid contact info | If able to obtain updated contact info |

FIG. 5

| Column | Description |
|---|---|
| contactSummaryID | Unique, autogenerated identifier |
| srcCustomerID | Unique customer identifier from management system database |
| srcRecallId | Unique recall identifier from management system database. Will be NULL for "other due customes" |
| lastApptTypeNR | When srcRecallId is Null, type of last appointment from management system database |
| lastApptDateNR | When srcRecallId is NULL, date of last appointment from management system database. When srcRecallId is NULL, the three fields srcCustomerId, lastApptDate, and lastApptType combine to uniquely identify an appointment that should be scheduled. |
| dueDate | Date appointment is due. If srcRecallId is non-NULL, obtained from management system recall table, otherwise derived based on lastApptDate, lastApptType, and accepted standards of case or office policies |
| dueFor | Text describing what the return appointment is for. Derived from management system recall table for recalls, or by rules for non-recall contacts. |
| scedulerId | Unique identifier of scheduler who is currently being prompted to contact this customer, or NULL if customer is not currently being contacted. |
| finalResult | Description |
| Column | Description |

FIG. 6

| Column | Description |
|---|---|
| contactDetailsId | Unique, autogenerated identifier |
| contactSummaryId | Unique contactSummary identifier (refer to FIG. 6) |
| schedulerId | Identifies scheduler who made this contact |
| contactDate | Date and time of contact |
| result | Result of contact (refer to FIG. 5) |

FIG. 7

METHOD AND APPARATUS FOR IDENTIFYING AND CONTACTING CUSTOMERS WHO ARE DUE FOR A VISIT BUT HAVE NOT SCHEDULED AN APPOINTMENT

TECHNICAL FIELD

The present invention relates to methods and apparatus for scheduling, and more particularly, to methods and apparatus for customer scheduling to recapture lost business by identifying and contacting customers who have not responded to reminders to schedule an appointment, or who are due back for an appointment based on accepted standards of care or office policies, but who have not yet been scheduled for an appointment.

BACKGROUND OF THE INVENTION

Many businesses rely on scheduled appointments to provide an agreed time and place to serve customers. In many cases, after serving a customer, a return appointment will be recommended for some time in the future. Often, an appointment is made for a return visit before the customer leaves the office. However, if the needed appointment is too far out, or if staff schedules are unreliable, or if a suitable appointment cannot be found quickly, then the office may instead choose to use a recall. A recall is a notice, sent to the customer prior to the desired appointment date, reminding the customer to call to schedule an appointment.

Many management systems that schedule customer appointments provide support for recall notices. Typically, these systems allow entry of a target date for the unscheduled appointment, which is associated with the customer, and some notes about the reason for the recall. On a regular basis, the management system is used to generate printed cards, letters or address labels, so that reminders to call for an appointment can be sent to the appropriate customers. Instead of printed reminders, automated calling systems are sometimes used to leave a recorded message requesting a return call to schedule an appointment.

There is another class of customers that are due back for a visit at a periodic interval based on accepted standards of care and office policies for a specific condition, but have not been scheduled for an appointment and are not set up in the management system to receive a reminder to do so. For example, glaucoma customers may require quarterly visits to manage intraocular pressures; diabetic customers may require an eye exam every six months; and healthy customers may require an annual eye exam. Sometimes, a customer may slip out of the office after one of these routine visits without a follow-up appointment or a recall being made. Other times an appointment is made, and then canceled or missed, and the customer then forgets to call for a new appointment. All of these events lead to a situation where a customer requires contact to schedule a needed visit.

Some management systems, particularly electronic medical records systems, store rules representing standards for periodic care, based on a customer's condition. However, these systems don't generally provide queries or reports covering the situations described above. Instead, these rules guide schedulers at the time that return appointments are made.

On the other hand, these systems often do provide a report or query which provides a list of customers who have not responded to recall notices, so that these customers can be contacted or reminded again. Unfortunately, a simple list of unresponsive customers is inadequate for schedulers involved in a shared, sustained effort to contact customers and schedule these appointments. Schedulers require a record of the times and dates of messages left so that additional messages are not left with the same customers until a sufficient time has elapsed as to warrant another contact. Further, schedulers require that as customers are contacted successfully and appointments are scheduled, these customers are deleted from the list so that these customers are not contacted again after an appointment is made.

These shortcomings make the process of contacting customers who have not responded to recall notices difficult enough that many offices choose not to make the effort, resulting in a substantial loss of business and profits. This invention overcomes these obstacles by automatically tracking which customers have been or are presently being contacted, so that multiple schedulers can work from the same list without making redundant calls to customers.

As of 2005, there were over 800 vendors selling practice management software, many of which support recalls and provide reports of customers who have not responded to recall notices. None of these systems provide the features described in this application to facilitate personally contacting customers to request appointments.

SUMMARY OF THE INVENTION

A first principal object of the present invention is to facilitate outbound calling as a means to schedule appointments with customers who have not responded to reminders to call for an appointment. This class of customers will hereafter be referred to as "recall due customers."

A second principal object is to facilitate outbound calling as a means to schedule appointments with customers who are due for a visit according to accepted standards of care or office policies, but who have not been scheduled for an appointment and are not set up in the management system to receive a reminder to do so. This class of customers will hereafter be referred to as "other due customers."

A third principal object is to enable multiple schedulers to conveniently work from the same list of customers without interfering with each other as they contact customers.

A fourth principal object is to automatically keep a record of customer contacts so that further contact can be appropriately timed or controlled to avoid redundant contacts with customers.

A fifth principal object is to sort the customer list and present customers to schedulers in an order that makes best use of scheduler time, for instance, by calling higher-paying customers before lower-paying customers.

The invention begins by querying the management system to determine the set of recall due customers and/or other due customers. This combined set will hereafter be referred to as "due customers." The resulting due customer set, or list, may be sorted or filtered based on the expected value of each appointment in order to maximize the return on outbound calls, or by provider and/or location in order to focus on filling specific schedules. Due customers are then presented to the scheduler via a computer apparatus, hereafter referred to as "contact program," along with the information necessary to contact the customer. The scheduler then attempts to contact the customer and schedule an appointment. Contact results, including a timestamp, are recorded in the contact system database via the contact program. The contact history is then used to prevent redundant or too frequent contacts.

According to a first aspect, the invention is a method for attempting to schedule an appointment for a customer in an office having one or more persons tasked with scheduling appointments for the office in an office management system.

The method includes the steps of: a) querying the office management system to determine a first class of customers whose appointments have not been scheduled despite reminding the customer at least once to schedule the appointment, b) prompting the one or more persons to make a first personal contact with a customer in the first class of customers by a predetermined means to attempt to schedule the appointment for the customer, c) personally contacting the customer to attempt to schedule the appointment, the personal contact being made by at least one of the one or more persons using the predetermined means, d) noting the results of the first personal contact, and e) noting the time of step c).

According to a second aspect, the invention is a method for attempting to schedule an appointment for a customer in an office having one or more persons tasked with scheduling appointments for the office in an office management system.

The method includes the steps of: a) querying the office management system to determine a first class of customers whose appointments have not been scheduled despite reminding the customer at least once to schedule the appointment, b) prompting the one or more persons to make a first personal contact with a customer in the first class of customers by a predetermined means to attempt to schedule the appointment for the customer, c) personally contacting the customer to attempt to schedule the appointment, the personal contact being made by at least one of the one or more persons using the predetermined means, d) noting the results of the first personal contact, and e) noting the time of step c).

The method further includes the steps of: f) querying the office management system to determine a second class of customers whose appointments have not been scheduled despite receiving a first personal contact at least a predetermined length of time before the present time, g) prompting the one or more persons to personally contact a customer in the second class of customers by a predetermined means to attempt to schedule the appointment for the customer, h) personally contacting the customer to attempt to schedule the appointment, the personal contact being made using the predetermined means by at least one of the one or more persons, i) noting the results of the contact, and j) noting the time of step h).

According to a third aspect, the invention is a method for attempting to schedule an appointment for a customer in an office having one or more persons tasked with scheduling appointments for the office in an office management system, the office management system describing each customer and appointment according to one or more attributes which influence profitability or office preferences.

The method includes the steps of: a) querying the office management system to determine a first class of customers whose appointments have not been scheduled despite reminding the customer at least once to schedule the appointment, b) sorting the first class of customers according to customer and appointment attributes, so that all customers whose appointments are more profitable or preferable are presented for contact before customers with less profitable or preferable attributes, c) prompting the one or more persons to personally contact a customer belonging to the first class of customers by a predetermined means to attempt to schedule the appointment for the customer, d) personally contacting the customer to attempt to schedule the appointment, the personal contact being made using the predetermined means by at least one of the one or more persons, e) noting the results of the contact, and f) noting the time of step d).

According to a fourth aspect, the invention is a method for attempting to schedule an appointment for a customer in an office having one or more persons tasked with scheduling appointments for the office in an office management system.

The method includes the steps of: a) querying the office management system to determine a first class of customers who are due back for a visit according to accepted standards of care or office policies, but have not been scheduled for an appointment, b) prompting the one or more persons to make a first personal contact with a customer in the first class of customers by a predetermined means to attempt to schedule the appointment for the customer, c) personally contacting the customer to attempt to schedule the appointment, the personal contact being made by at least one of the one or more persons using the predetermined means, d) noting the results of the first personal contact, and e) noting the time of step d).

According to a fifth aspect, the invention is a method for attempting to schedule an appointment for a customer in an office having one or more persons tasked with scheduling appointments for the office in an office management system.

The method includes the steps of: a) querying the office management system to determine a first class of customers who are due back for a visit according to accepted standards of care or office policies, but have not been scheduled for an appointment, b) prompting the one or more persons to make a first personal contact with a customer in the first class of customers by a predetermined means to attempt to schedule the appointment for the customer, c) personally contacting the customer to attempt to schedule the appointment, the personal contact being made by at least one of the one or more persons using the predetermined means, d) noting the results of the first personal contact, and e) noting the time of step d).

The invention further includes the steps of f) querying the office management system to determine a second class of customers whose appointments have not been scheduled despite receiving a first personal contact at least a predetermined length of time before the present time, g) prompting the one or more persons to personally contact a customer in the second class of customers by a predetermined means to attempt to schedule the appointment for the customer, h) personally contacting the customer to attempt to schedule the appointment, the personal contact being made using the predetermined means by at least one of the one or more persons, i) noting the results of the contact, and j) noting the time of step h).

According to a sixth aspect, the invention is a method for attempting to schedule an appointment for a customer in an office having one or more persons tasked with scheduling appointments for the office in an office management system, the office management system describing each customer and appointment according to one or more attributes which influence profitability or office preferences.

The invention includes the steps of a) querying the office management system to determine a first class of customers who are due back for a visit according to accepted standards of care or office policies, but have not been scheduled for an appointment, b) sorting the first class of customers according to customer and appointment attributes, so that all customers whose appointments are more profitable or preferable are presented for contact before customers with less profitable or preferable attributes, c) prompting the one or more persons to personally contact a customer belonging to the first class of customers by a predetermined means to attempt to schedule the appointment for the customer, d) personally contacting the customer to attempt to schedule the appointment, the personal contact being made using the predetermined means by at least one of the one or more persons, e) noting the results of the contact, and f) noting the time of step d).

DETAILED DESCRIPTION OF THE PREFERRED EMBODIMENT OF THE INVENTION

The following detailed description will be made in the context of the broad steps of a method. It will be understood that the steps of the method described can be accomplished by means of a conventional computer system, including a display device.

The broad steps are: querying the office management system to determine which customers have not responded to recall notices ("recall due customers"), or who are due for a visit according to accepted standards of care or office policies, but have not scheduled an appointment ("other due customers"); prompting a scheduler to personally contact one of these customers to attempt to schedule the appointment; personally contacting the customer to attempt to schedule the appointment; recording the results of the contact in a contact system database; and automatically recording the time and date of contact into the contact system database. Appointments are made using the existing management system's scheduling user interface.

Figure 1:
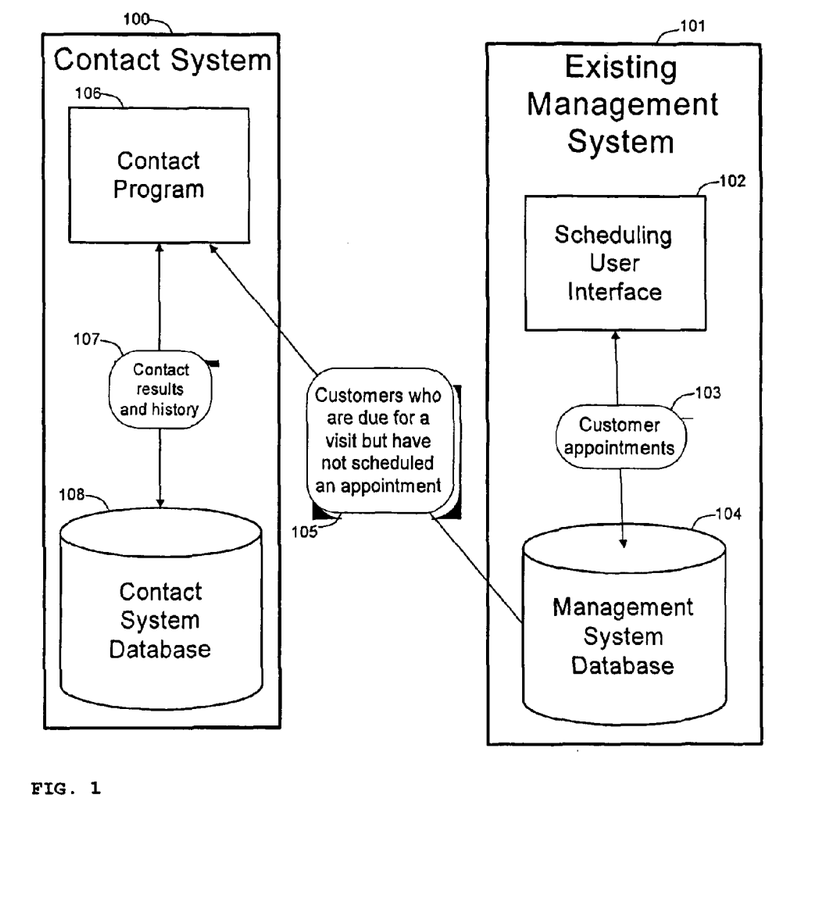
FIG. 1 is a block diagram showing the contact system as it interacts with the existing management system.

FIG. 1 is a block diagram showing the contact system as it interacts with the existing management system. The contact system 100, which programs a conventional computer, consists of a contact program 106 and a contact system database 108. The contact system interfaces with an existing management system 101, which also programs a conventional computer. The existing management system consists of a scheduling user interface 102 and a management system database 104. The scheduling user interface 102 draws customer appointments 103 from the management system database 104, and writes new appointments 103 into the management system database 104. The contact program 106 queries customers who are due for a visit but have not scheduled an appointment 105 and prompts one or more users to contact these customers. The contact results and history 107 are stored into the contact system database 108. The contact program 106 queries the contact system database 108 to avoid contacting customers redundantly or too frequently.

Figure 5:
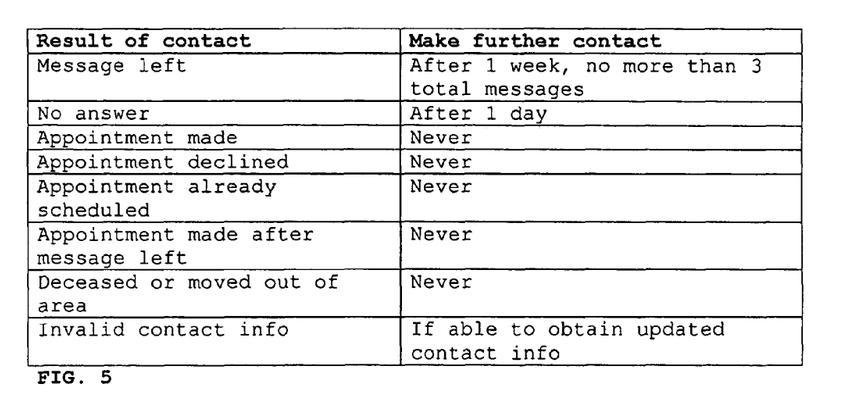
FIG. 5 is an exemplary table of contact results and rules for further contact.
Figure 6:
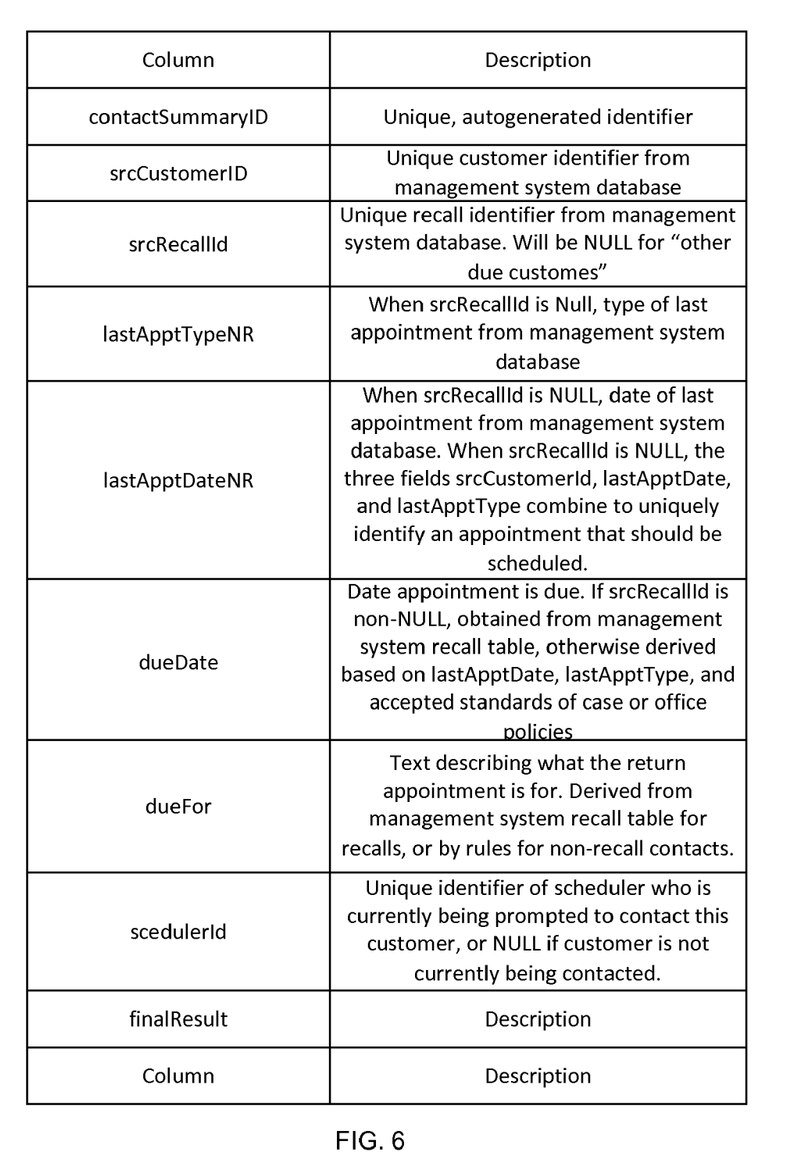
FIG. 6 is a list of fields in the contact system database's contactSummary table, which contains the details of each customer to be contacted.

Querying the Office Management System to Determine which Customers are Due for a Visit but have not Scheduled an Appointment FIG. 6 is a list of fields in the contact system database's contactSummary table, which contains the details of each customer to be contacted ("due customer"). FIG. 5 is an exemplary table of contact results and rules for further contact.

An exemplary procedure for identifying due customers follows:

Once daily:
1) Query the management system database and contact system database to see if any due customers have scheduled an appointment since a message was left in a contact attempt, and update finalResult in contact system database's contactSummary table (FIG. 6) to "appointment made after message left" (FIG. 5) as appropriate.
2) Query the management system database for due customers that are not yet in the contact system database, and add these to the contact system database's contactSummary table (FIG. 6).

Step 2, query the management system database for due customers, is further explained below.

There are two types of due customers: recall due customers and other due customers. The following sections explain how to query for each.

Querying the Office Management System for Recall Due Customers

There are many different management systems, each with its own database schema, so the exact query will vary from system to system. However, most of these systems are built on standard database products, such as Microsoft SQL Server (produced by Microsoft Corporation of Redmond, Wash.), which can be queried using standard, documented query language.

A query to the management system database 104 is executed via the contact program 106 which enumerates all customers who have not responded to recall notices. The query returns information required to contact the customer and other information that may be helpful when contacting the customer, including customer name, customer identification number, customer phone number, recall notes/reason, doctor name, which office they were last seen at, and the dates they were last seen, expected back, and last sent a recall notice. Based on user preferences, this query can be sorted from highest to lowest paying customers to maximize the return on outbound call time, or by provider so that specific staff members' schedules will be filled first.

In order to reduce the number of calls to customers who have moved, changed doctors, or passed away, it is best to query only for customers whose recall dates were within the past year or some other similar time threshold.

In order to avoid calling customers who have just received recall notices, the query is further limited to customers who were sent a recall notice no more recently than six weeks ago, or some other similar time threshold.

If scheduling staff have not reliably closed out recall notices as appointments have been made, then the resulting data set returned in response to the query will include customers who have responded to recalls. In this case, a simple heuristic, such as whether the customer scheduled an appointment after the recall was entered into the system, will greatly reduce the number of redundant contacts made. However, not all return appointments fulfill the specific purpose for a particular recall notice. For example, a customer with glaucoma who is set up for a recall to return in six months for a glaucoma check and returns two months later for a glasses check would still need to return again for his glaucoma check. Therefore, filtering based on customers who have not scheduled an appointment since entering the recall notice will cause some number of customers to be dropped from the contact list that should have received calls. However, if the problems caused by calling customers who have already responded to recall notices are serious enough, or if there are many recall prompts in the system which have not been closed out properly, then this tradeoff may be appropriate.

Querying the Office Management System for Other Due Customers

The first step is to determine the schedule of care required for each condition. For example, glaucoma customers may require quarterly visits; diabetic customers may require semi-annual exams; and healthy customers may require annual exams. These ideal visit periods must be built into queries specific to each condition.

The next step is to build a query for each condition that returns the list of customers known to have that condition. In a management system which contains diagnostic results, such as an electronic medical records system, those diagnostic results will provide this information. Without diagnostic results, one good solution is to query for customers who have previously been in for appointment types that indicate the condition. For example, a customer who has come in for a diabetic eye exam can be assumed to have diabetes, and a customer who has come in repeatedly for a pressure check might be assumed to have glaucoma. Appointment notes can also be parsed for keywords such as "diabetic" or "glaucoma" although this method may confuse screenings with regular care visits, which could lead to unnecessarily contacting customers who were screened for, but not diagnosed with, a particular disease such as glaucoma.

Finally, this query must be modified to exclude customers who meet any of the following conditions:
  1. The customer is not yet due for another visit (the last visit for this condition was within the accepted period for regular visits).
  2. The customer is already scheduled for a visit for this condition in the future.
  3. The customer is set up to receive a recall notice for a visit for this condition.
  4. The customer is deceased or otherwise inactive.

Sorting Customers Based on Expected Appointment Value

In order to provide the best return on outbound calling time, customers can be sorted based on expected appointment value. Expected appointment value is the amount of revenue expected from a given appointment, based on customer and appointment attributes contained in the management system. The following sections describe how to calculate expected appointment value using information such as payor class, provider, appointment type and attendance history. These attributes can either be used individually or combined to calculate expected appointment value.

Sorting Customers Based on Average Billings Per Visit

In order to sort customers based on how well they pay, it is necessary to calculate the average value of a visit according to some identifying attribute, such as the payor class of a customer. Management systems will usually have a table which identifies the payor for each customer, and another table that identifies the payor class that each payor belongs to, which provides broad categories of insurance types, such as Medicare, preferred provider, Medicaid, and so on. These tables must be joined in order to assign each customer to a payor class. If no payor class table exists, then the individual payors may be used instead.

Figure 2:
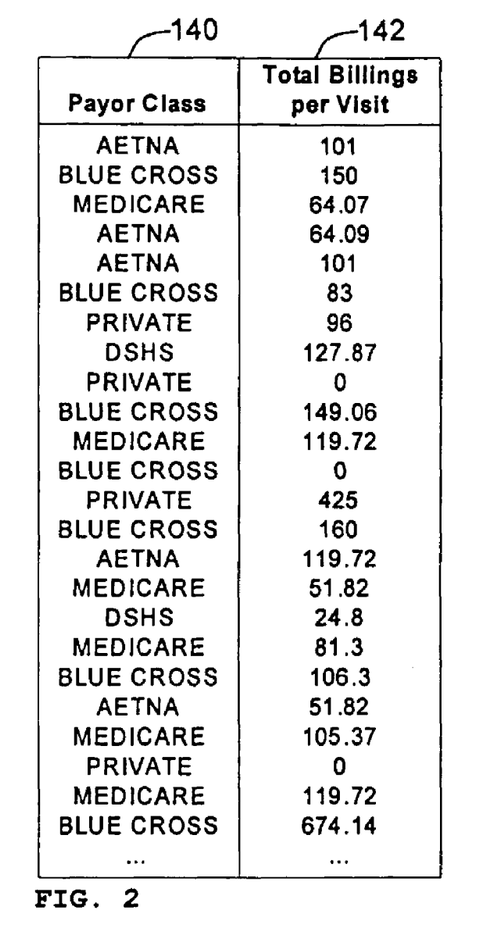
FIG. 2 is an exemplary table of total billings per visit by payor class.

Because multiple items may be billed per visit, it is necessary to create a table of total billings per visit before calculating the average billings per visit. For example, a single visit may result in separate billings for diagnostic tests, physician fees and facility fees. These must be summed to calculate the total billings per visit. Calculate the total billings per visit by aggregating billings based on a common visit code or activity date for each customer, and join the results with the payor class table, creating a table of <payor class (column 140), total billings per visit (column 142)> pairs. FIG. 2 is an exemplary table of total billings per visit by payor class.

Figure 3:
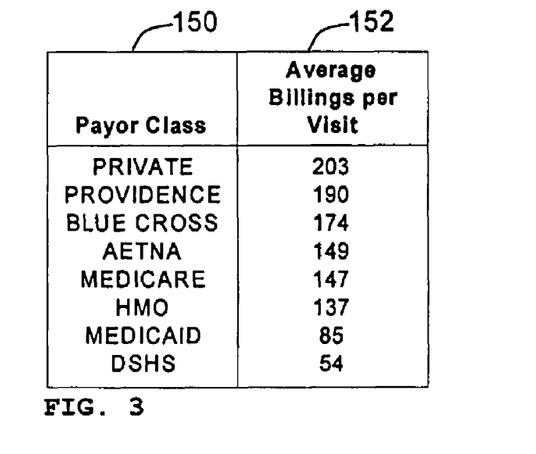
FIG. 3 is an exemplary table showing the average billings per visit, by payor class.

Next, calculate the average billings per visit, grouping by payor class, in order to determine the average billings per visit for each payor class. FIG. 3 is an exemplary table showing the average billings per visit, by payor class. The payor classes are shown in column 150 and the average billing for each respective payor class is shown is column 152.

Finally, join the resulting table with the list of recall due customers, and sort descending by the average billings per visit column. This will give you a prioritized list of customers, such that the first customers called belong to payor classes which pay more per visit, on average, than other payor classes.

Sorting Customers Based on Appointment Type or Provider

A more accurate estimate of appointment value can be obtained by considering appointment type and provider in addition to payor, when sorting customers. To do this, follow the same procedure as above, using combinations of attributes to build average billings per visit. Instead of simply grouping by payor when calculating total and average billings per visit, group them by payor, provider and appointment type. Sort descending by average billings per visit, and use the resulting order of payor, provider and appointment type combinations to sort customers before presenting customers for contact.

For example, if private-paying customers seeing Dr. Aikes for cataract surgery pay more on average than Medicaid customers seeing Dr. Paynes for new glasses, then private-paying customers who are due back to see Dr. Aikes for cataract surgery would be presented for contact before Medicaid customers due back to see Dr. Paynes for new glasses.

This same scheme can be used to combine any number of attributes, as long as there is adequate data in the system to calculate meaningful average visit values. If there is insufficient data, select fewer attributes to sort by.

Converting Average Billings Per Visit to Expected Visit Value Based on Attendance History The average billings per visit can be converted to expected visit value based on the customer's attendance history, in order to give preference to customers who show up consistently for appointments. Given adequate attendance history, this will provide a more accurate expected appointment value.

First, calculate the percentage of appointments attended for each customer without late cancellation or failure to show up for the appointment. To do this, total up the number of appointments made for each customer recorded in the management system, including appointments which were subsequently canceled or rescheduled. Calculate the number of slots consumed by each customer by subtracting the number of appointments which were canceled or rescheduled with adequate notice (for example, at least 24 hours) to fill these slots with other customers. Next, calculate the number of slots wasted by adding up the number of times each customer failed to show for an appointment or cancelled or rescheduled without giving adequate notice to fill the slot with another customer (use the same 24 hour threshold as used to calculate the number of slots consumed but calculate reschedules and cancellations with less than 24 hours notice). Subtract the number of wasted slots from the total number of slots consumed, and divide the result by the total number of slots consumed to provide the percentage attendance value for each customer. This average attendance value can be used alone, as with the average billings per visit column, by sorting customers in descending order based on their attendance. Alternatively, it can be multiplied by the average billings per visit column, to weight the billings per visit value prior to its use to prioritize contacts.

For example, assume a particular customer has scheduled a total of seven appointments during his history with the clinic. Three of these were canceled or rescheduled at least 24 hours in advance. Thus, the customer has consumed four appointment slots. Of these, one was canceled two hours prior to the appointment, but the customer has never failed to show up for an appointment without first canceling. Hence, of the four appointments consumed, one was wasted. The percentage attendance value for this customer is three (the number of slots consumed minus the number wasted) divided by four (the number consumed), or 75%.

In order to avoid giving too great weight to short attendance histories, it may be desirable to set some minimum number of slots consumed (such as 3) below which customers are simply assigned the average attendance history value for all customers as a group, rather than their own.

Filtering the List Based on Specific Criteria

Customers can also be filtered by customer or appointment attributes, in order to focus on filling specific providers' schedules, specific provider-location combinations, specific locations, appointment types, and so on. To filter based on office preferences, present the user a list of attribute values, such as providers or locations, and allow them to select those to include or exclude, and then filter the customer list accordingly.

One particularly valuable form of filtering is to filter by provider, based on the number of appointment slots about to expire unused for each provider, so that outbound calling reduces the number of wasted slots. To do this, count the number of free slots within some brief period in the future, such as three days. Sort customers such that those customers who are due to see providers with the most empty slots are presented first. Alternatively, in order to focus outbound calling exclusively on filling slots that would otherwise expire unused in a very busy office, filter the customer list so that only customers who are due to see a provider with free slots in the next three days are presented for contact.

Figure 4:
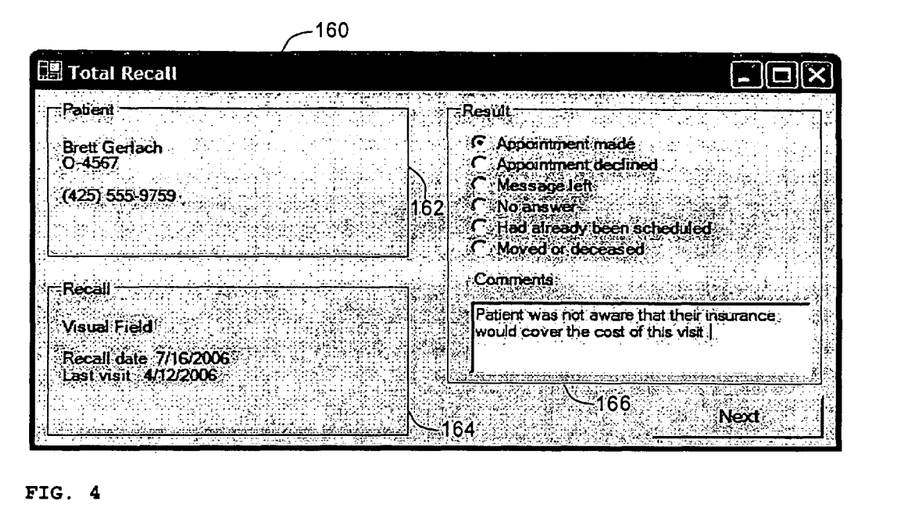
FIG. 4 is an exemplary program, which prompts the scheduler to call the customer for an appointment.

Prompting a Scheduler to Personally Contact a Due Customer to Attempt to Schedule the Appointment A customer is presented to the scheduler, or optionally, a list is provided from which to select a customer. FIG. 4 is an exemplary program which prompts the scheduler to call the customer for an appointment. This program (in window 160) presents (in field 162) customer contact information, such as the customer name, phone number, and a unique customer identification number that can be used to look up the customer in the management system. It also presents information about the due appointment (in field 164), such as the purpose and due date, and the date of the last visit. Finally, it provides a set of options to record the result (in field 166) of the personal contact, such as appointment made, appointment declined, message left, no answer, etc. After the scheduler calls the due customer, she chooses the appropriate result, makes any comments appropriate to the call, and presses the Next button to record these results and automatically record a timestamp. The contact system then presents the next due customer to be contacted.

The following is the specific logic required to correctly present data to one or more schedulers via this program:

In the contact program, query the contact system database for the next customer to contact. For convenience, a query may provide a list of customers which can be displayed to allow the scheduler to choose whom to contact. When a customer is selected (either automatically or via user selection):

1. If any of the following are true, abort contact and query for next customer:
    a. customer is already currently being contacted by another scheduler.
    b. customer has scheduled an appointment since a message was left in a prior contact attempt. If so, update contact result to "appointment made after message left" (FIG. 5) in contact system database.
    c. customer has scheduled an appointment without a message left in any prior contact attempt. If so, update contact result to "appointment already scheduled" (FIG. 5) in contact system database.
    d. customer has invalid contact information. If so, update contact result to "invalid contact info" (FIG. 5) in contact system database. Optionally, query the internet for possible updated contact information.
2. Mark customer as currently being contacted in contact system database (to prevent redundant contacts when multiple schedulers are working simultaneously).
3. Display customer's contact and due appointment information Personally Contacting the Customer to Attempt to Schedule the Appointment Using the customer contact information provided by the program described above, the scheduler attempts to contact the customer and schedule an appointment. If the customer cannot be contacted, the scheduler may leave a message requesting a return call.

Alternatively, phone software may be used which leaves a message when no human is contacted, and turns the call over to a scheduler when the customer answers.

Recording the Results of the Contact

Figure 7:
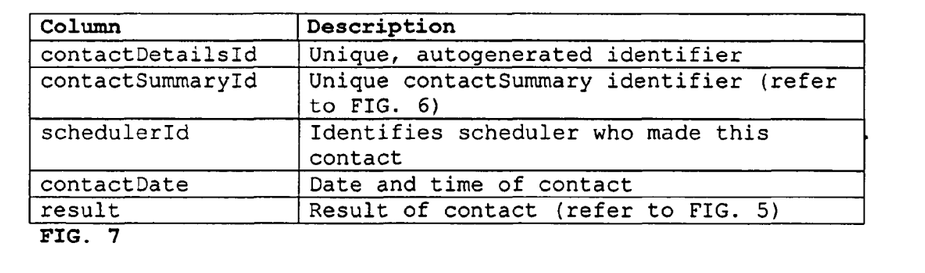
FIG. 7 is a list of fields in the contact system database's contactDetails table, which contains the details of each attempted contact.

After the scheduler has attempted to contact the customer, the scheduler indicates the result of the contact, such as whether an appointment was made, a message was left, the appointment was declined, and so on. This information is stored into the contact system database, and the "currently being contacted" flag is updated. FIG. 7 is a list of fields in the contact system database's contactDetails table, which contains the details of each attempted contact. There is a one-to-many relationship between the contactSummary table and the contactDetails table.

Responding to Incorrect Phone Numbers

When the user indicates the contact result was an incorrect phone number, the contact system can use a web service, such as anywho.com or dexonline.com, to look up phone numbers for matching customer names in the geographical area, and present these to the user, so the user can try these alternate numbers and correct the incorrect number in the system. Because phone listings don't include all the names in a family, this lookup should include the name of the customer and the name of the person who is responsible to pay the bill, as listed in the management database.

Automatically Recording the Time and Date of Contact

When the scheduler indicates the contact result, the time and date of contact are also automatically recorded into the contact system database. Until a sufficient time has passed to warrant another call according to the rules in FIG. 5, this customer will not be presented to schedulers for another contact.

Integrating the Contact System and the Management System

Instead of separating the contact system and the management system into two separate programs, each with its own database, the two systems can also be combined, with the contact system built into the management system as a feature of that system. In this case, the same database can be used to store the contact system contact results and history, as well as the customer appointment information and other management system data.

SUMMARY

It is not always possible or desirable to schedule return appointments with customers as they leave. Instead, customers may be reminded to call for an appointment when the time approaches for them to return. Often, customers fail to heed these reminders, and so a system is required which supports contacting these customers after they have failed to respond to requests to call. In addition, customers who are due for an appointment according to accepted standards of care but who have not scheduled an appointment need to be identified and contacted in order to schedule appointments. The present invention offers the support necessary to efficiently identify and contact these customers, so that they can be scheduled for an appointment. By contacting these customers, professionals can fill empty slots in their schedules, thus improving revenues and profits, while simultaneously offering a higher level of service to customers.

While the foregoing is a detailed description of the preferred embodiment of the invention, there are many alternative embodiments of the invention that would occur to those skilled in the art and which are within the scope of the present invention. Accordingly, the present invention is to be determined by the following claims.

The invention claimed is:

1. A method for scheduling an appointment for a customer in an office having one or more persons tasked with scheduling appointments for the office in a computer-implemented office management system, the computer-implemented office management system describing each customer and appointment according to one or more attributes which influence profitability or office preferences and storing information in an office management system electronic database, comprising the steps of:
    a) querying by a contact management program executing on a computer the office management system electronic database to determine a first class of customers whose appointments have not been scheduled despite reminding the customer at least once to schedule the appointment,
    b) sorting the first class of customers according to an expected appointment value, so that customers whose appointments have a higher expected appointment value are presented for contact before customers whose appointments have a lower expected appointment value, wherein the expected appointment value comprises an amount of revenue expected from the appointment that is to be scheduled, wherein the amount of revenue expected from the appointment to be scheduled is based on an average billings per visit and an individual attendance history of each of the customers in the first class of customers,
    c) displaying contact information associated with a customer belonging to the first class of customers on a computer screen to prompt the one or more persons to personally contact the named customer to schedule the appointment for the customer, wherein the expected appointment value associated with the customer being displayed to the one or more persons is higher than the expected appointment value of customers in the first class of customers that have not been displayed,
    d) personally contacting the customer to schedule the appointment, the personal contact being made by at least one of the one or more persons,
    e) noting the results of the personal contact in an electronic database, and
    f) noting the time of step d).

2. The method according to claim 1, wherein step b) further consists of determining the average billings per visit based on the type of insurance or payment class to which the customer belongs.

3. The method according to claim 2, wherein step d) further comprises:
    in response to the contact result indicating an incorrect phone number, looking up and presenting a list of phone numbers for the customer to a person making the personal contact.

4. The method according to claim 1, wherein step d) further comprises:
    in response to the contact result indicating an incorrect phone number, looking up and presenting a list of phone numbers for the customer to a person making the personal contact.

5. The method according to claim 1, where step b) further consists of sorting the first class of customers by at least one of a provider or location based on which of the at least one provider or location has the lightest schedule.

6. The method according to claim 5, wherein step d) further comprises:
    in response to the contact result indicating an incorrect phone number, looking up and presenting a list of phone numbers for the customer to a person making the personal contact.

7. The method according to claim 1, where step b) further consists of sorting the first class of customers based on an appointment type, so that specific slots dedicated to specific appointment types can be filled.

8. The method according to claim 1, where step b) further consists of sorting the first class of customers based on an appointment type, so that appointment types which yield the highest average revenue are scheduled first.

9. A method for scheduling an appointment for a customer in an office having one or more persons tasked with scheduling appointments for the office in a computer-implemented office management system, the computer-implemented office management system describing each customer and appointment according to one or more attributes which influence profitability or office preferences and including an office management system electronic database, comprising the steps of:
    a) querying by a contact management computer program executing on a computer the office management system electronic database to determine a first class of customers who are due back for a visit according to accepted standards of care or office policies, but have not been scheduled for an appointment,
    b) sorting the first class of customers according to an expected appointment value, so that customers whose appointments have a higher expected appointment value are presented for contact before customers whose appointments have a lower expected appointment value, wherein the expected appointment value comprises an amount of revenue expected from the appointment that is to be scheduled, wherein the amount of revenue expected from the appointment to be scheduled is based on an average billings per visit and an individual attendance history of each of the customers in the first class of customers, c) displaying contact information associated with a customer belonging to the first class of customers on a computer screen to prompt one or more persons to personally contact the named customer belonging to the first class of customers to schedule the appointment for the customer, wherein the expected appointment value associated with the customer being displayed to the one or more persons is higher than the expected appointment value of customers in the first class of customers that have not been displayed, d) personally contacting the customer to schedule the appointment, the personal contact being made by at least one of the one or more persons, e) noting the results of the contact in an electronic database, and f) noting the time of step d).

10. The method according to claim 9, wherein step b) further consists of determining the average billings per visit based on the type of insurance or payment class to which the customer belongs.

11. The method according to claim 9, where step b) further consists of sorting the first class of customers by at least one of a provider or location based on which of the at least one provider or location has the lightest schedule.

12. The method according to claim 9, where step b) further consists of sorting the first class of customers based on an appointment type, so that specific slots dedicated to specific appointment types can be filled.

13. The method according to claim 9, where step b) further consists of sorting the first class of customers based on an appointment type, so that appointment types which yield the highest average revenue are scheduled first.

14. The method according to claim 9, wherein the office is an office selected from a class of offices including a medical office, a dental office, and a law office.

15. An apparatus for scheduling for scheduling an appointment for a customer in an office having one or more persons tasked with scheduling appointments for the office in an office management system, the office management system describing each customer and appointment according to one or more attributes which influence profitability or office preferences, comprising:

a) a computer programmed to query the office management system to determine a first class of customers whose appointments have not been scheduled despite reminding the customer at least once to schedule the appointment, b) the computer programmed to sort the first class of customers according to an expected appointment value, so that customers whose appointments have a higher expected appointment value are presented for contact before customers whose appointments have a lower expected appointment value, wherein the expected appointment value comprises an amount of revenue expected from the appointment that is to be scheduled, wherein the amount of revenue expected from the appointment to be scheduled is based on an average billings per visit and an individual attendance history of each of the customers in the first class of customers, c) the computer programmed to prompt one or more persons to personally contact a customer belonging to the first class of customers to schedule the appointment for the customer, wherein the expected appointment value associated with the customer to be personally contacted is higher than the expected appointment value of customers in the first class of customers that have not been displayed, and d) the computer programmed to record the results and time of the contact.

16. The apparatus according to claim 15, wherein the computer programmed to sort the first class of customers determines the average billings per visit based on the type of insurance or payment class to which the customer belongs.

17. The apparatus according to claim 15, where the computer programmed to sort the first class of customers is further programmed to sort the first class of customers based on an appointment type, so that specific slots dedicated to specific appointment types can be filled.

18. The apparatus according to claim 15, where the computer programmed to sort the first class of customers is further programmed to sort the first class of customers by at least one of a provider or location based on which of the at least one provider or location has the lightest schedule.

19. The apparatus according to claim 15, where the computer programmed to sort the first class of customers is further programmed to sort the first class of customers based on an appointment type, so that appointment types which yield the highest average revenue are scheduled first.

20. An apparatus for scheduling an appointment for a customer in an office having one or more persons tasked with scheduling appointments for the office in an office management system, the office management system describing each customer and appointment according to one or more attributes which influence profitability or office preferences, comprising:

a) a computer programmed to query the office management system to determine a first class of customers who are due back for a visit according to accepted standards of care or office policies, but have not been scheduled for an appointment, b) the computer programmed to sort the first class of customers according to an expected appointment value, so that customers whose appointments have a higher expected appointment value are presented for contact before customers whose appointments have a lower expected appointment value, wherein the expected appointment value comprises an amount of revenue expected from the appointment that is to be scheduled, wherein the amount of revenue expected from the appointment to be scheduled is based on an average billings per visit and an individual attendance history of each of the customers in the first class of customers, c) the computer programmed to prompt one or more persons to personally contact a customer belonging to the first class of customers to schedule the appointment for the customer, wherein the expected appointment value associated with the customer to be personally contacted is higher than the expected appointment value of customers in the first class of customers that have not been displayed, and d) the computer programmed to record the results and time of the contact.

21. The apparatus according to claim 20, wherein the computer programmed to sort the first class of customers further determines the average billings per visit based on the type of insurance or payment class to which the customer belongs.

22. The apparatus according to claim 20, where the computer programmed to sort the first class of customers further sorts the first class of customers by at least one of a provider or location based on which of the at least one provider and/or location has the lightest schedule.

23. The apparatus according to claim 20, where the computer programmed to sort the first class of customers further sorts the first class of customers based on an appointment type, so that specific slots dedicated to specific appointment types can be filled.

24. The apparatus according to claim 20, where the computer programmed to sort the first class of customers further sorts the first class of customers based on an appointment type, so that appointment types which yield the highest average revenue are scheduled first.

25. The method according to claim 1, wherein the office is an office selected from a class of offices including a medical office, a dental office, and a law office.

26. The method according to claim 15, wherein the office is an office selected from a class of offices including a medical office, a dental office, and a law office.

27. The method according to claim 20, wherein the office is an office selected from a class of offices including a medical office, a dental office, and a law office.

* * * * *